United States Patent
Killion et al.

Patent Number: 6,159,238
Date of Patent: Dec. 12, 2000

[54] STENT HAVING VARIABLE PROPERTIES AND METHOD OF ITS USE

[75] Inventors: Douglas P. Killion, Maple Grove; James R. Lininger, New Hope, both of Minn.

[73] Assignee: SciMed Life Systems, Inc, Maple Grove, Minn.

[21] Appl. No.: 09/314,658

[22] Filed: May 19, 1999

Related U.S. Application Data

[62] Division of application No. 09/034,249, Mar. 4, 1998, Pat. No. 5,938,697.

[51] Int. Cl.$^7$ .................................................. A61F 2/06
[52] U.S. Cl. ........................ 623/1.11; 128/898; 623/1.3
[58] Field of Search ................. 623/1.15, 1.3, 623/1.31, 1.1, 1.23; 128/898

[56] References Cited

U.S. PATENT DOCUMENTS

| | | | |
|---|---|---|---|
| 4,743,251 | 5/1988 | Barra | 623/1.11 |
| 5,064,435 | 11/1991 | Porter | 623/1.11 |
| 5,383,892 | 1/1995 | Cardon et al. | 623/1.11 |
| 5,449,373 | 9/1995 | Pinchuk | 623/1.11 |
| 5,575,818 | 11/1996 | Pinchuk | 623/1.11 |
| 5,683,411 | 11/1997 | Kavteladze et al. | 623/1.11 |
| 5,693,086 | 12/1997 | Goicoechea et al. | 623/1.11 |
| 5,725,549 | 3/1998 | Lam | 623/1.11 |
| 5,741,133 | 4/1998 | Frid | 623/1.11 |
| 5,741,333 | 4/1998 | Frid | 623/1 |
| 5,755,769 | 5/1998 | Richard et al. | 623/1.11 |
| 5,776,162 | 7/1998 | Kleshinski . | |
| 5,800,508 | 9/1998 | Goicoechea et al. | 623/1.11 |
| 5,800,514 | 9/1998 | Nunez et al. | 623/1.11 |
| 5,807,404 | 9/1998 | Richter . | |
| 5,817,126 | 10/1998 | Imran . | |
| 5,817,152 | 10/1998 | Birdsall et al. . | |
| 5,824,059 | 10/1998 | Wijay | 623/1.11 |
| 5,827,321 | 10/1998 | Roubin et al. | 606/195 |
| 5,836,966 | 11/1998 | St. Germain | 606/198 |
| 5,855,600 | 1/1999 | Alt . | |
| 5,861,027 | 1/1999 | Trapp . | |
| 5,868,780 | 2/1999 | Lashinski et al. . | |
| 5,868,783 | 2/1999 | Tower . | |
| 5,876,448 | 3/1999 | Thompson et al. . | |
| 5,902,317 | 5/1999 | Kleshinski et al. . | |
| 5,913,895 | 6/1999 | Burpee et al. . | |
| 5,922,019 | 7/1999 | Hankh et al. . | |

FOREIGN PATENT DOCUMENTS

| | | |
|---|---|---|
| WO 94/15548 | 7/1994 | WIPO . |
| WO 96/25124 | 8/1996 | WIPO . |

OTHER PUBLICATIONS

"*Handbook of Bioengineering*" Chapter 21, By Richard Shaloh & Shu Chin, McGraw–Hil Book Company, 1987.

*Primary Examiner*—David H. Willse
*Assistant Examiner*—Suzette J. Jackson
*Attorney, Agent, or Firm*—Vidas, Arrett & Steinkraus, P.A.

[57] ABSTRACT

A stent and method of its use, the stent in its expanded configuration, exhibiting varying outward radial force along its length. In use, the expanded stent is of a tapered configuration which provides greater force in vessel regions requiring greater force and less force in regions requiring less. In particular the stent is useful in the ostium regions and at areas of bifurcation in vessels. Varying force over the length of the stent is achieved by varying the number of elements, the density of elements, the thickness of the elements making up the stent body, and maintaining a substantially metal to artery ratio in the expanded stent over its length.

4 Claims, 5 Drawing Sheets

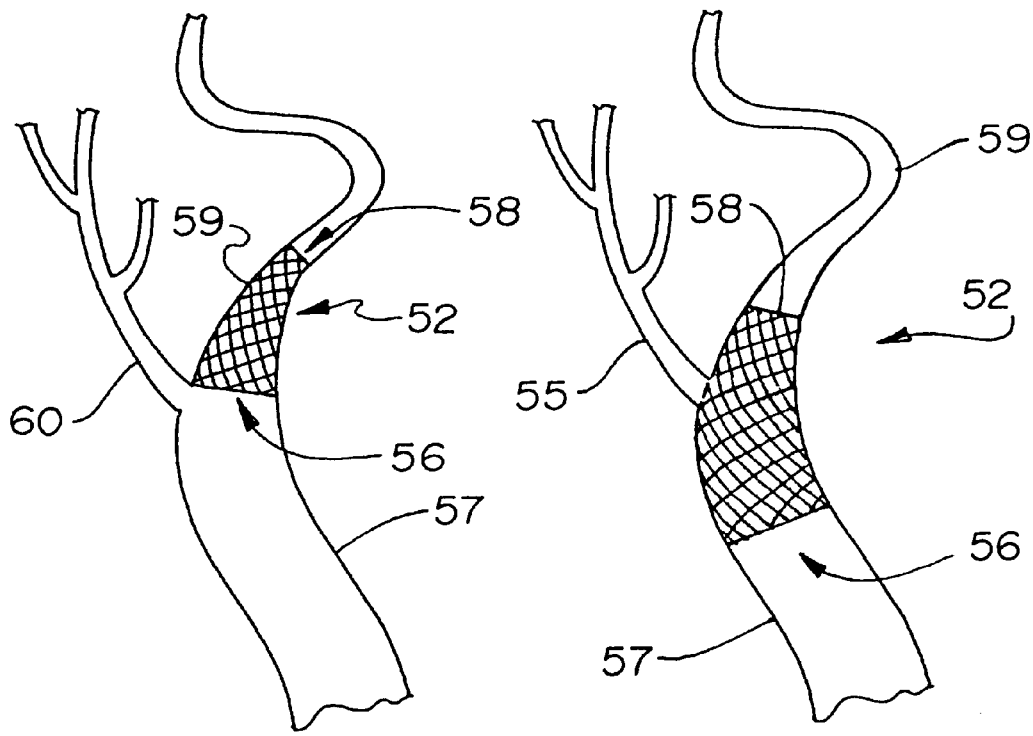

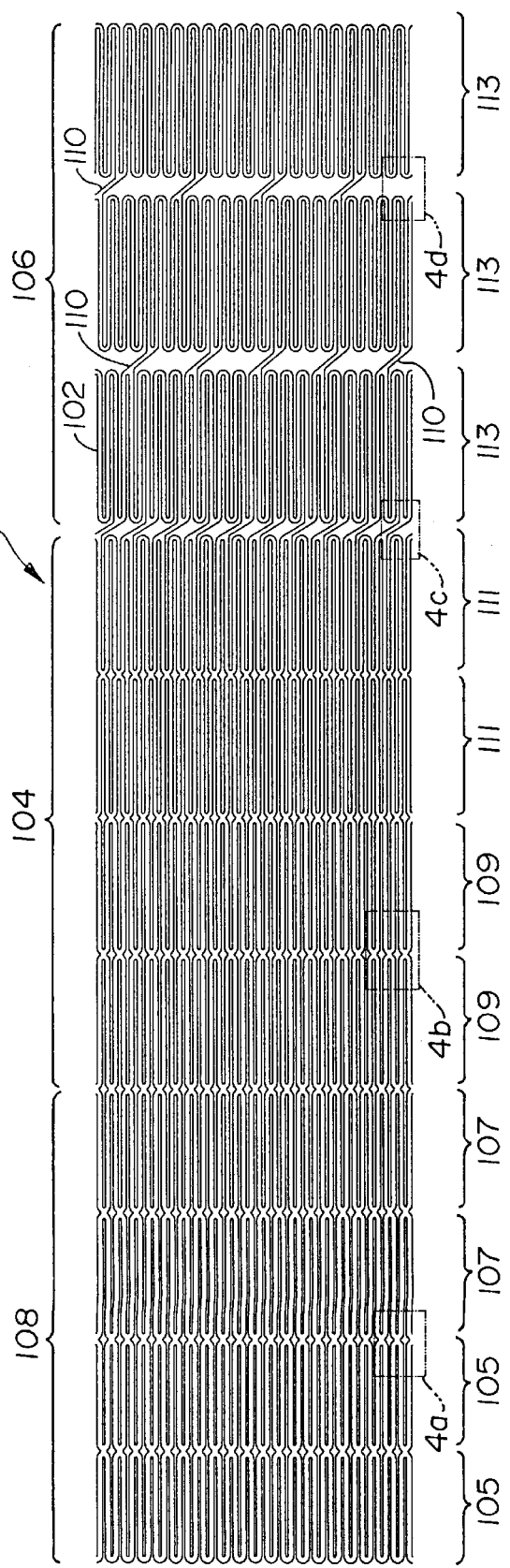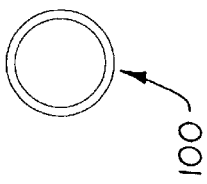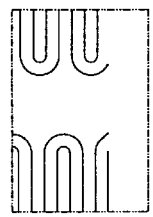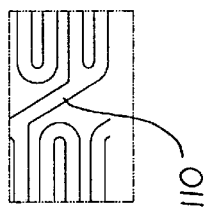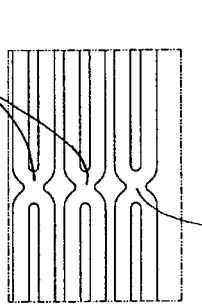

STENT HAVING VARIABLE PROPERTIES AND METHOD OF ITS USE

CROSS REFERENCE TO CO-PENDING APPLICATION

This application is a Divisional of U.S. application Ser. No. 09/034,249, filed Mar. 4, 1998, now U.S. Pat. No. 5,938,697 which is incorporated herein in its entirety by reference.

FIELD OF THE INVENTION

The invention relates generally to medical devices and their use. More specifically, the invention relates to stents for holding vessels such as arteries open to flow, particularly in the regions of bifurcations.

BACKGROUND OF THE INVENTION

Stents are radially expandable endoprostheses which are typically intravascular implants capable of being implanted transluminally and enlarged radially after being introduced percutaneously. They have also been implanted in urinary tracts and bile ducts. They are used to reinforce body vessels and to prevent restenosis following angioplasty in the vascular system. They may be self-expanding or expanded by an internal radial force, such as when mounted on a balloon.

Stents are generally tubular devices for insertion into tubular vessel regions. Balloon expandable stents require mounting over a balloon, positioning, and inflation of the balloon to expand the stent radially outward. Self-expanding stents expand into place when unconstrained, without requiring assistance from a balloon. A self-expanding stent is biased so as to expand upon release from the delivery catheter.

A vessel having a stenosis may be viewed as an inwardly protruding arcuate addition of hardened material to a cylindrical vessel wall, where the stenosed region presents a somewhat rigid body attached along, and to, the elastic wall. The stenosis presents resistance to any expansion of the vessel in the region bridged by the stenosis. Stenoses vary in composition, for example, in the degree of calcification, and therefore vary in properties as well.

The arcuate geometry of any stenoses present a variation in resistance along the vessel axis to stent outward radial force. Specifically, stenosed vessel resistance is often greatest toward the middle, lessening toward the ends, with a rapid decrease at the start of healthy vessel tissue.

In some instances, as in regions of bifurcation, stenoses are believed to be flow related phenomena, see Chapter 21 of the *"Handbook of Bioengineering"* (Richard Shaloh & Shu Chin, McGraw-Hill Book Company, 1987) which discusses atherosclerosis at vascular bifurcations.

The left and right common carotid arteries are typical of such vascular bifurcations. These arteries are the principal arteries of the head and neck. Both of the common carotid arteries are quite similar and divide at a carotid bifurcation or bulb into an external carotid artery and an internal carotid artery. In the region of the carotid bulb and the ostium of the internal carotid artery, stenoses present a particular problem for carotid stenting due to the large tapering of the vessel interior from the common carotid artery (both the left and the right) to the internal carotid artery. The region of the carotid bifurcation or bulb happens to be where stenoses most often occur, particularly in the region of the ostium to the internal carotid artery in both of the carotid arteries. Self-expanding stents are generally preferred for carotid stenting due to the anatomical location being subject to external compression.

A conventional self-expanding stent optimally has a length greater than the length of the stenosed region to be kept open. Current stents present a substantially uniform outward radial force and a uniform resistance to compression along their length. Currently, stents do not vary these forces to match vessel geometries or resistances. A constant force stent, i.e., prior art stents, with sufficient force to maintain an open channel within a stenosed vessel and to resist compression, has greater force than necessary in the healthy vessel portion distal to the stenosis. The stent end may thus flare outward, protruding into, and possibly irritating non-stenosed tissue.

Stenoses can occur in vessel regions having asymmetric geometry lying on either side of the stenosis. One example of this is the ostium of an internal carotid artery, having a wide opening converging into a narrower artery. A conventional stent placed in the region of the ostium would provide substantially uniform outward radial force over a non-uniform vessel diameter, that is, the force provided would be greater in a small diameter than in a larger diameter. If this force is properly matched for the smaller vessel region, it is likely less than optimal for the larger region. Conversely, if this force is properly matched for the larger vessel region, it is likely more than optimal for the smaller vessel region.

What would be desirable, and has not heretofore been provided, is a tapered stent capable of providing sufficient force to keep a vessel open within a rebounding stenosis, while providing only necessary force against healthy, non-stenosed vessel regions. What else has not been provided is a tapered stent providing necessary, but only necessary force (outward force and compression resistance) along a stenosis in a vessel region having non-uniform vessel diameter on either side of the stenosis. This is provided by the tapered stents of this invention which exhibit differing radial force, cell size, geometry, flexibility and which provide substantially more constant metal to artery ratio (M/A) over their length. M/A is the ratio of the metal surface area of a stent to the surface area of the vessel or the like that the stent is covering.

SUMMARY OF THE INVENTION

The present invention, in a preferred embodiment, includes a self-expanding stent of shape-memory metal having a tubular or cylindrical shaped structure in the unexpanded condition and a tapered tubular or cylindrical structure in the expanded or memorized condition, and in which the radial force varies longitudinally along the length of the stent. Also, its resistance to compression varies with length. Additionally, the cell design making up the stent is closed where force and good plaque coverage and support is required and open where flexibility is required. Additionally, the metal to artery ratio is substantially more constant over the length of the stent when it is expanded. One such stent is constructed of Nickel-Titanium alloy (nitinol). Other shape memory metals may be used. In one embodiment, the stent is constructed and arranged so that the outward radial force is greater in the center and lesser at both ends. In another embodiment, the stent is constructed and arranged so that the outward radial force is greater at one end and less at the opposite end. Such stents are suitable for placement in stenosed and narrowing vessel regions such as the carotid bifurcation and the ostial area associated therewith.

The stents of the invention may achieve a variation in radial force along their length by including in the stent structural elements which intersect at connections having more metal in regions requiring more radial force and less metal in regions requiring less radial force. The amount of intersection metal or strut member metal can be varied by varying the size of the intersection area or the size of the struts. Greater or fewer connectors actually are used to vary the flexibility along the length of the stent more than increasing radial force. In a preferred embodiment, the stent structure is formed by laser cutting a Nitinol tube, leaving a greater strut width and shorter length in regions requiring greater outward radial force and compression resistance.

The struts of the invention are also characterized by the fact that they are constructed and arranged to present a substantially more constant metal to artery ratio over their length in the expanded condition, i.e., expanded to a tapered shape.

The stent structure in a preferred embodiment includes a series of serpentine annular segments which are aligned to provide a tubular structure. The segments are interconnected longitudinally. A desired radial force can be varied by varying the stent strut dimensions in this and other embodiments. In one embodiment, stent regions requiring greater radial force have wider and shorter struts than regions requiring less force. The number of connectors between segments can also be varied for this purpose. It is also obtained by varying strut length and spacing and overall size. Another control is cell design per se. Closed cells provide greater plaque coverage and support than open cells. Closed cells are generally connected to cells in adjoining segments of the stent whereas open cells are not so connected. These factors also provide control over properties such as flexibility and conformability. Cell geometry, i.e., closed and open, is used to provide good plaque support in the region of the stenoses (closed) and less support (open) and more flexibility to either side of the stenoses. Also, closed cell structure may be used to bridge the origin of the external carotid artery or any other vessel side branch opening.

Generally speaking it is desirable to provide a stent of this invention with the aforementioned radial force which is variable over stent length in a predetermined arrangement; cell design which is closed in the area where the stent contacts plaque of a stenoses and more open where the stent contacts healthy vessel tissue; flexibility and conformability which is arranged to vary in a predetermined arrangement over the length of the stent, in both unexpanded and expanded condition.

Stents made in accordance with the present invention can provide an outward radial force more closely matching the local force requirements in a tapered vessel. In particular, the stents provide greater force only where required at a stenosis, without providing too much force in the region of healthy tissue. The stents provide an expanded geometry more closely tailored to the requirements of a tapering vessel region. They are preferably stiff and strong at the proximal large diameter end or middle and weak and more flexible at the distal smaller diameter end to provide strain relief and prevent kinking of the vessel distal to the stent. The proximal end may also be flexible.

A stent of the invention with variable properties along its length also applies to balloon expandable stents that can be used across bifurcations with large diameter change by dilating with a smaller balloon distally and a larger balloon proximally.

This invention is also concerned with a method for treating stenoses in vessel bifurcation regions involving the use of a stent of the type described above.

BRIEF DESCRIPTION OF THE FIGURES

FIG. 1 is a schematic showing of a scenario 1 for carotid stenting;

FIG. 3 is a schematic profile view of an expanded, tapered stent for use in the scenario 1 of FIG. 1;

FIG. 4 is a flat plan view in detail of an unexpanded stent of the type shown schematically in FIG. 3, including exemplary dimensions;

FIGS. 4a, 4b, 4c and 4d are detail showings of portions of FIG. 4;

FIG. 5 is an end view of the stent of FIG. 4;

FIG. 7 is a schematic of a scenario 2 for carotid stenting;

FIG. 8 is a schematic profile view of an expanded, tapered stent for use in the scenario 2 of FIG. 7;

DETAILED DESCRIPTION OF THE INVENTION

Figure 2A:
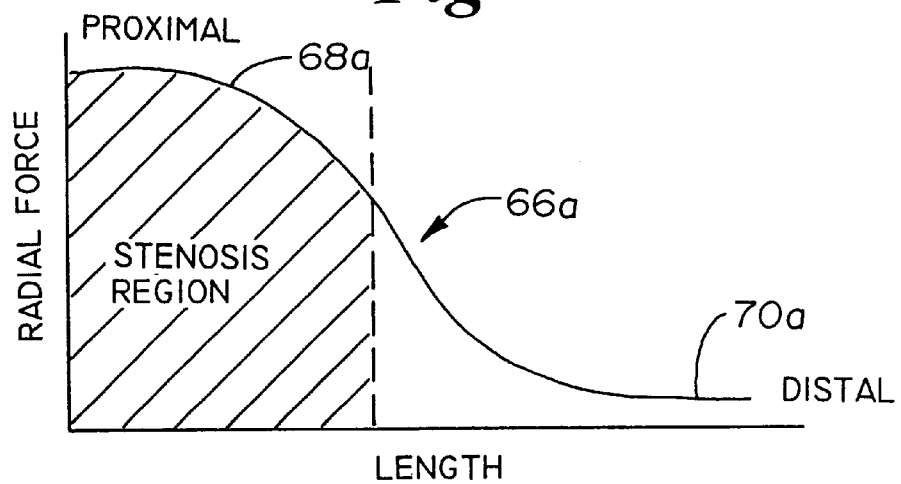
FIGS. 2a and 2b are plots of force versus length of improved stents for placement in FIGS. 1 and 7 respectively, i.e., an ostial stent and a bifurcation stent.

FIG. 1 illustrates a narrowing vessel 52, such as the internal carotid artery, having a wide region 56, a narrowed region 58, and a stenosis (not shown) somewhere in between, i.e., in the cross-hatched region. The narrowing vessel of FIG. 1 illustrates the geometry as found in an ostium at the bifurcation of the left common carotid 57, where blood flows from the left common carotid artery 57 into the left internal carotid artery 59. The bifurcation also opens into the left external carotid artery 60. An ordinary stent with sufficient force to hold open the wide region 56 would have greater force than necessary to hold open the narrowed region 58.

FIG. 2a illustrates a plot 66a of outward radial force F along a tapered, expanded stent length L for a stent embodying the present invention. The stent has a greater force in end region 68a than at the opposite end region 70a. A tapered stent having the force curve of FIG. 2a is suitable for bridging a stenosis as illustrated in FIG. 1, having sufficient force to hold open the wide region 56 of a vessel and less force in the narrow healthy tissue region 58 of the vessel, where less is required.

FIG. 3 illustrates in schematic fashion a preferred nitinol stent embodiment of the invention producing a force distribution as illustrated in FIG. 2. Self-expanding stent 80 includes a conformable distal end 82 for contacting healthy vessel tissue, and a stiffer, closed-cell proximal region 88 for providing increased plaque support. It has upon expansion a tapered diameter as shown. For example, a 0.236 inch distal diameter and a 0.354 inch proximal diameter might be typical. These dimensions can be varied. Stent 80 is positioned on the distal end of a delivery catheter, covered with a removable sheath, advanced to a stenosis to be crossed, and exposed for self-expansion by removal of the sheath. Stent 80 expands radially to its memorized tapered shape pushing against the stenosis and vessel wall.

FIG. 4 illustrates in more detail the nitinol unexpanded stent embodiment of FIG. 3 in flat plan view as a stent 100, having a middle region 104 and end regions 106 and 108.

Stent 100 has a tubular shape, shown in FIG. 5, formed of several serpentine segments 105, 107, 109, 111 and 113, having a zig-zag pattern, each segment radially encircling a portion of stent 100. Referring again to FIG. 4, segments 113 are longitudinally interconnected by connectors 110, whereas the serpentine segments 105, 107, 109 and 111 are all interconnected as shown in FIGS. 4a and 4b by direct connections 112. A preferred material for constructing stent 100 is Nitinol. In this embodiment, the stent is formed by laser cutting a continuous-walled nitinol tube of diameter 0.081 inches having a wall thickness of 0.006 inches, leaving only the stent structure as shown. Typical dimensions of various elements of the stent are shown in the Figure by way of example.

Figure 6:
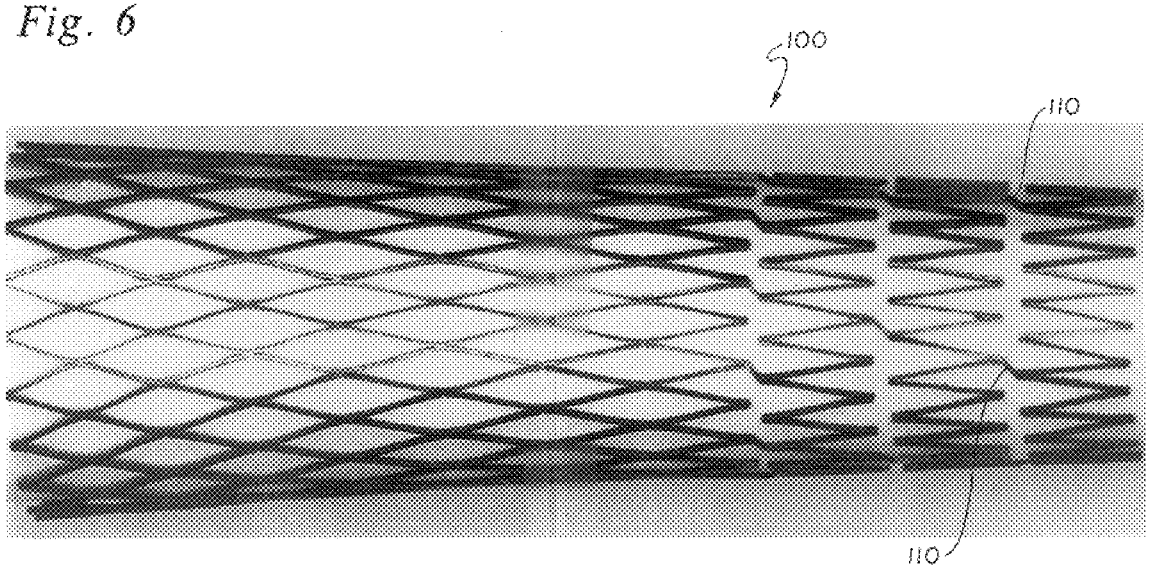
FIG. 6 is a view showing the stent of FIG. 4 in the expanded condition.

Referring now to FIG. 6, the stent of FIG. 4 is shown expanded and tapered. Since nitinol is a shape memory metal it can be formed into the shape and size shown in FIG. 4, placed over a tapered tool and expanded to a desired enlarged shape and size, such as the 0.236 inch distal diameter and 0.354 inch proximal diameter previously mentioned, heated to a high temperature such as 500° C. to give it the memorized size and shape on the tool. The stent is then removed from the tool and can be compressed for mounting on the delivery catheter.

By starting with a stent of nitinol having the dimensions set forth in FIG. 4, the expanded condition provides a stent having the desirable properties described hereinbefore with reference to FIG. 3. All dimensions in the Figure are in inches. Of course, this is but one example of a stent according to the invention.

FIG. 7, similarly to FIG. 1, illustrates a narrowing vessel 52 having a wide region 56, a narrowed region 58, a branching vessel 55 and a stenosis (not shown) somewhere in between regions 56 and 58, i.e., the cross hatched region. Again, narrowing vessel of FIG. 7 illustrates the geometry as found at the bifurcation of the left common carotid artery 57, where blood flows from the left common carotid artery 57 into the left internal carotid artery 59.

Figure 2B:
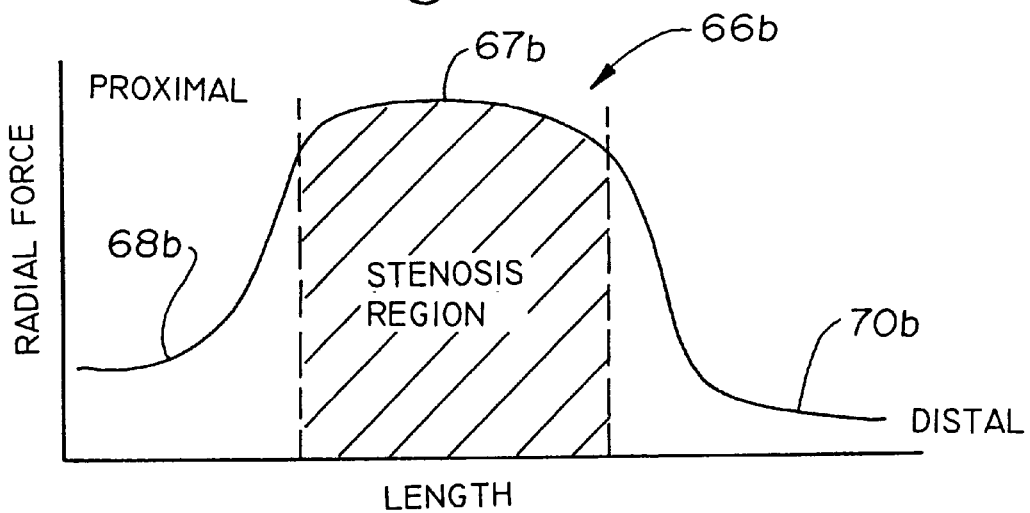

FIG. 2b illustrates a plot 66b of outward radial force F along a tapered, expandable stent length L for a stent embodying the present invention. The stent has a greater force in its middle region 67b than at its end regions 68b and 70b. A tapered stent having the force curve of FIG. 2b is suitable for bridging a stenosis as illustrated in FIG. 7, having sufficient force to hold open the wide region at the ostium of internal carotid 59 and less force in healthy tissue at wide end 56 and narrow end 58.

A stent for use in this cross hatched region will have properties such as those to be described with reference to FIGS. 8 and 9, which will be different from the stent previously described with reference to FIGS. 1–6.

Referring now to the FIG. 8 schematic, stent 80 includes a middle region 84 and end regions 86 and 87. The amount of radial force exerted per unit length of stent is greater in regions having shorter and wider struts. As schematically illustrated in FIG. 8, stent 80 has shorter and wider struts in center region 84 than in end regions 86 and 87. Thus, stent 80 has a greater outward radial force and compression resistance in center region 84 than in end regions 86 and 87 making it particularly useful for stenting in the cross-hatched region of FIG. 7.

Figure 9:
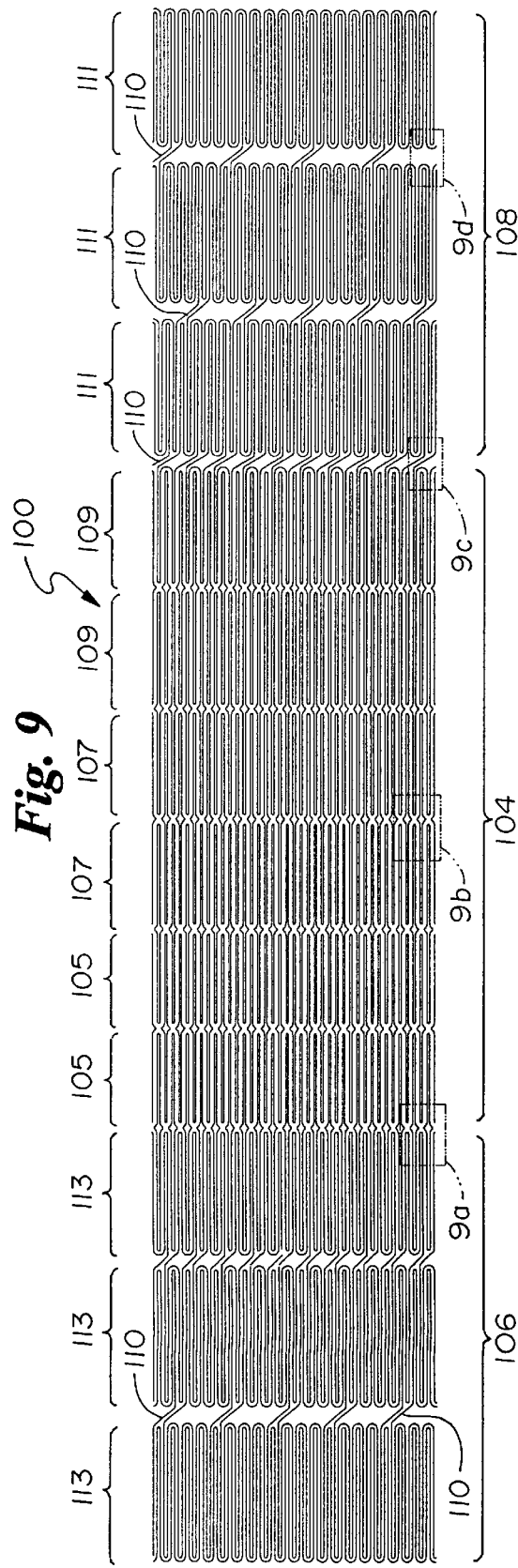
FIG. 9 is a flat plan view in detail of an unexpanded stent of the type shown schematically in FIG. 8, including exemplary dimension.
Figure 10:
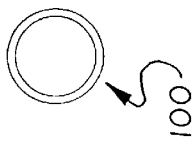
FIG. 10 is an end view of the stent of FIG. 9.
Figure 9D:
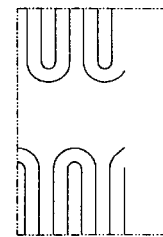
Figure 9C:
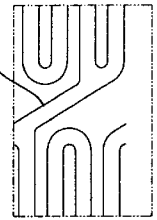
Figure 9B:
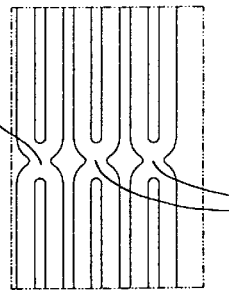
Figure 9A:
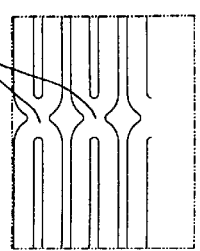

FIG. 9 illustrates in more detail the nitinol unexpanded stent embodiment of FIG. 8 in flat plan view as a stent 100 having a middle region 104 and end regions 106 and 108. Stent 100 has a tubular shape, shown in FIG. 10, formed of several serpentine segments 105, 107, 109, 111 and 113, having a zig-zag pattern, each segment radially encircling a portion of stent 100. Segments 111 and 113 are respectively longitudinally interconnected by several connectors 110 whereas serpentine segments 105, 107 and 109 are all interconnected as shown in detail in FIGS. 9a and 9b by direct connections 112. This embodiment is also formed by laser cutting a continuous-walled nitinol tube of diameter 0.081 inches having a wall thickness of 0.006 inches, leaving only the stent structure as shown. Typical dimensions of various elements of the stent are shown in FIG. 9 by way of example.

Similarly to the stent embodiment of FIG. 4 as expanded to a tapered shape shown in FIG. 6, the stent of FIG. 9 can be provided with a tapered memorized shape in the expanded condition. The stent will exhibit all of the desirable proportions heretofore described, particularly as discussed with reference to FIG. 2b. All dimensions in FIG. 9 are in inches.

The present invention provides a stent which when expanded to its tapered configuration, provides a radial force varied along stent length for use in tapered anatomies. The stent has been described, in use, as bridging stenosed vessel regions for illustrative purposes. Another use in maintaining open channels through otherwise restricted body conduits. Stents used for other purposes are explicitly within the scope of the invention.

It should be noted that although self-expanding stents have been shown herein to illustrate the present invention, so called balloon expandable stents can also include the variable radial force feature as described herein. In the case of balloon expandable stents, however, these forces in general will be less than are necessary to expand the stent and thus the balloon will be used as known to those skilled in the art to complete the expansion of the stent. To obtain the tapered shape, two balloons of different diameter may be used to expand each end of the stent. These balloon expandable stents may be advantageously deployed in areas of a vessel such as at an ostium where a stent having more rigid or heavy members is desirable in the region of the stenosis, and enhanced flexibility in the distal portion of the stent is desired. For example, a balloon expandable stent can be made of stainless steel to the design and dimensions shown in either FIG. 4 or FIG. 9. It should be understood therefore, that balloon expandable stents are also within the scope of the present invention.

In use, a stent of the self-expanding type, in unexpanded form, is placed on a delivery catheter and covered with a retractable sheath. The catheter is introduced into a vessel and advanced to a region of bifurcation (ostium or bifurcation placement). The sheath is retracted, typically by pulling it in the proximal direction, to expose the stent. The stent then self-expands to contact the vessel wall and stenosis. In the case of a self-expanding stent such as the nitinol type described herein, the stent expands to the tapered configuration upon being exposed and exhibits the desired proportion described hereinbefore. A sheath is typically used for constraining a self-expanding stent. A balloon expandable stent is typically crimped on to the balloon and not covered by a sheath. In the case of a non-self-expanding stent, a balloon or other radial force means is inflated within the stent to expand it. In the case of the stents described herein, two balloons may be used sequentially to accomplish this. For example, a small balloon may be used to expand the stent at the small diameter end of the tapered configuration. Then, a larger balloon may be used to expand the stents at the large end of the tapered configuration. The catheter(s) are withdrawn, leaving the stent implanted in the vessel. The method is adaptable depending on whether an ostial version or a bifurcation version of the stent is being implanted.

Numerous characteristics and advantages of the invention covered by this application have been set forth in the foregoing description. It will be understood, however, that this disclosure is, in many aspects, only illustrative. Changes may be made in details, particularly in matters of shape, size, and arrangement of parts and in materials without exceeding the scope of the invention. The invention's scope is, of course, defined in the language in which the appended claims are expressed.

What is claimed is as follows:

1. A method of stenting a bifurcation region or ostial region in a blood vessel, comprising the steps of:

providing a stent having an unexpanded configuration and an expanded configuration, the latter having a length and a varying diameter along said length comprising a tapered tubular shaped metallic structure, said structure having a radially outward biased force and compression resistance, said force varying along said length in a predetermined manner, said tapered tubular structure having a first end region of largest diameter, a middle region of smaller diameter, and a second end region of smallest diameter, wherein said outward biased force is weaker in said first end region, stronger in said middle region than in said first region, and weaker in said second end region than in said middle region; introducing the stent into a catheter; inserting the catheter and stent into an implantation region at bifurcation or ostium of a vessel; expanding the stent to an enlarged diameter of a tapered configuration in support of the vessel wherein the aforementioned properties are exhibited, and removing the catheter leaving the stent implanted in the vessel.

2. The method of claim 1 wherein the stent is implanted in the bifurcation region of the common carotid artery, extending across the opening into the external carotid artery and into the internal carotid artery, the end of largest diameter being in the common carotid artery and the end of smallest diameter being in the internal carotid artery.

3. The method of claim 1 wherein the stent is formed of a shape memory material so as to be self-expanding, the stent structure having an unexpanded configuration and an expanded memorized configuration, the unexpanded configuration having an average diameter less than that of the expanded configuration, the expanded configuration having a diameter which varies along the length of the stent from a first end region, to a middle region, and to a second end region, wherein the second configuration diameter is smaller in said first end region, larger in said middle region than in said first region, and largest in said second end region than in said middle region or said first end region.

4. The method of claim 3 wherein the stent is implanted in the internal carotid with the end of largest diameter at the ostium thereof and the end of smallest diameter in healthy tissue downstream of the ostium.

* * * * *